United States Patent [19]

Hicks

[11] Patent Number: 5,198,894
[45] Date of Patent: Mar. 30, 1993

[54] DRAPE FOR ENDOSCOPE

[76] Inventor: John W. Hicks, 312 Howard St., Northboro, Mass. 01532

[21] Appl. No.: 764,820

[22] Filed: Sep. 24, 1991

[51] Int. Cl.⁵ .......................... H04N 7/18; A51B 1/04
[52] U.S. Cl. .......................................... 358/98; 128/4; 206/438
[58] Field of Search .................. 358/100, 98, 229; 128/4-6; 206/363, 438

[56] References Cited

U.S. PATENT DOCUMENTS

| | | | |
|---|---|---|---|
| 4,522,196 | 6/1985 | Cunningham et al. | 128/4 |
| 4,757,381 | 7/1988 | Cooper et al. | 358/225 X |
| 4,991,006 | 2/1991 | Wood | 358/100 |
| 5,010,876 | 4/1991 | Henley et al. | 206/438 X |

*Primary Examiner*—Victor R. Kostak
*Attorney, Agent, or Firm*—Samuels, Gauthier & Stevens

[57] ABSTRACT

An endoscope having a sleeve-like drape secured in a retracted position at the proximal end of the endoscope. The proximal end of the endoscope is secured to a CCD camera, the drape is extended to telescope over and envelope the camera such that the resulting outer surface of the drape in its extended position remains sterile.

4 Claims, 1 Drawing Sheet

DRAPE FOR ENDOSCOPE

BACKGROUND AND BRIEF SUMMARY OF THE INVENTION

The present invention relates to an endoscsope structure which allows a CCD camera to be secured to the proximal end of the endoscope in a sterile environment at the location where the endoscope exits the body cavity.

The transmission of light through thin fibers of glass or plastic have permitted a variety of instruments for the visualization of otherwise inaccessible organs and tissues inside the human body. Such instruments are broadly referred to as endoscopes and have been useful in the diagnosis and treatment of, for example, gastro intestinal and respiratory diseases.

In recent years, thin, flexible optical fibers have allowed for the remote viewing, photography, biopsy and surgery of organs and tissues. Such thin, flexible optical fibers, also known as fiber optics, are incorporated in endoscopes to enable the transmission of light to illuminate the internal space being viewed and/or enabling the object so illuminated to be viewed. Generally, the viewing capability is accomplished by aligning multiple fibers of that the relative position of each fiber is the same at each end of the bundle. The methods and apparatus of transmitting the images thereon is well known.

In addition to light and image transmission, endoscopes frequently have auxiliary channels through which fluids can pass, either to or from the observation site or through which implements and tools can be remotely controlled. In addition to the above, fiber optics are used in guiding laser radiation for applications in surgery, fluorescent methods of diagnosis and high intensity illumination. The fiber optics and endoscopes have also been applied to the development of a variety of transducers for the measurement and monitoring of parameters, such as blood flow, temperature, pressure and the like.

Typical endoscopes presently include a bundle of fiber optics, each having a light transmitting core and an outer cladding. The light enters the end of the core and through internal reflections passes down the core to the other end. A multiplicity of such fiber optics may be gathered together in a bundle along which light passes down the core to the other end. A second bundle, arranged in a coherent manner, may also be incorporated to provide a means of viewing the illuminated area at the distal end of the endoscope. The illuminating bundle, the visualizing bundle and the auxiliary channels, if any, are gathered together in a multi-lumen or hollow cylindrical sheath.

The proximal end of the endoscope usually has associated with it a video camera to read the optical signal. Usually a CCD camera, say less than about 1 inch in diameter is used. It is preferred to place the camera as near as possible to the location where the endoscope exits the body. However, when this is done the camera must be sterilized before each use or it must be covered with a sterile shroud or drape. Because the optical signal must go from the endoscope to the interior of the camera, this presents a window problem.

The present invention overcomes this problem by combining a sterile drape with a sterile endoscope.

Broadly the invention comprises an endoscope having a sleeve-like drape secured in a retracted position at the proximal end of the endoscope. The proximal end of the endoscope is secured to a CCD camera. The drape is extended to telescope over and envelop the camera. The drape can extend over the camera and along the cable associated with the camera as far as necessary. That is, either out of the sterile operating region or until it meets and overlaps another sterile drape.

DESCRIPTION OF THE PREFERRED EMBODIMENT(S)

Endoscopic CCD camera combinations are well known in the art and need not be described in detail for an understanding of the present invention.

Figure 1:
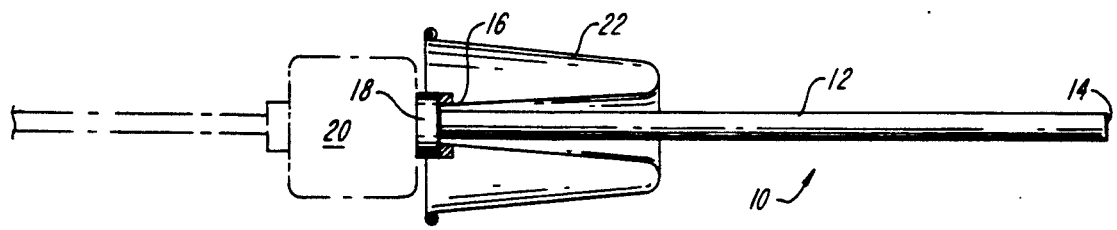
FIG. 1 is a side schematic view of an endoscope embodying the invention with a drape in a retracted position.

Referring to FIG. 1, an endoscope 10 is a multifiber encased in an outer protective sheath 12. The endoscope comprises a distal end 14 and a proximal end 16. The proximal end 16 is characterized by a circular mounting flange 18 secured to the sheath 12. A CCD camera 20 is in optical communication with the end 16. The camera 20 is secured to the flange 18.

Secured to the underside of the flange 18, such as by adhesives, is a standard, sterile, sleeve-like drape 22, such as a polyethylene sleeve.

As shown in FIG. 1, the drape is folded and in a retracted position.

Figure 2:
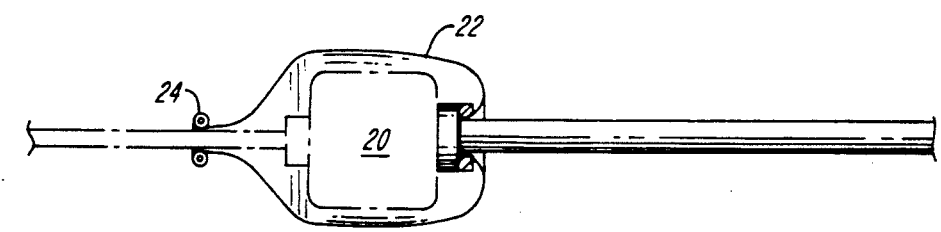
FIG. 2 is the endoscope of FIG. 1 with the drape in its extended position.

Referring to FIG. 2, after the camera 20 has been secured to the endoscope 10, the drape 22 is pulled to an extended position to telescope over and envelop the camera.

It is joined to another surgical drape 24 which envelops the camera cable. The drapes may be sealed to one another by adhesives.

Figure 3:
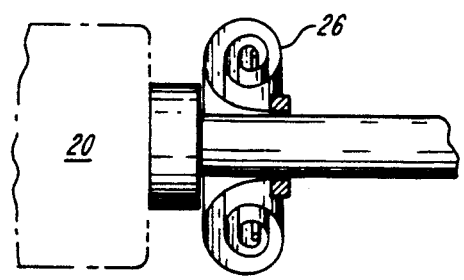
FIG. 3 is a schematic of an alternative embodiment of the invention.

In FIG. 3 an alternative embodiment of the invention is shown wherein a sterile sleeve-like drape 26 is secured at the end of the endoscope as in FIG. 1, but the drape is in a rolled configuration, such as a condom. The endoscope is attached, as for FIGS. 1 and 2, and then the drape is pulled over or rolled over the camera and over the cable, again telescoping and enveloping the camera and cable.

With the endoscope of the present invention the camera does not have to be sterilized and although a surgical drape is used the optical signal does not have to pass through a sterile window.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described my invention, what I now claim is:

1. In a system comprising an endoscope having a sheath, a camera in optical communication with the proximal end of the endoscope, and a cable extending from the camera, the improvement which comprises:

a sterile sleeve-like drape secured at the proximal end of the endoscope, the drape retracted in reference to the camera and adapted to be extended to telescope over and envelope the camera, the interface between the proximal end of the endoscope and the camera being free of sterile material the drape in its retracted position having an outer surface and an inner surface, the inner surface and outer surface of the drape reversing when the drape is in its extended position such that when the drape is moved to its extended position, the outer surface remains sterile.

2. The system of claim 1 wherein the drape is folded in a retracted position.

3. The system of claim 1 wherein the drape is rolled in a retracted position.

4. The system of claims 1, 2 or 3 wherein the proximal end includes a flange and the drape is secured to the flange.

* * * * *